(12) United States Patent
Benning

(10) Patent No.: US 8,601,630 B2
(45) Date of Patent: Dec. 10, 2013

(54) LINEAR BEARING USING ROLLING LEAF SPRINGS

(75) Inventor: Wolter F. Benning, Seattle, WA (US)

(73) Assignee: Koninklijke Philips N.V., Eindhoven (NL)

( * ) Notice: Subject to any disclaimer, the term of this patent is extended or adjusted under 35 U.S.C. 154(b) by 8 days.

(21) Appl. No.: 12/995,725

(22) PCT Filed: Jun. 8, 2009

(86) PCT No.: PCT/IB2009/052425
§ 371 (c)(1),
(2), (4) Date: Dec. 2, 2010

(87) PCT Pub. No.: WO2009/156886
PCT Pub. Date: Dec. 30, 2009

(65) Prior Publication Data
US 2011/0099738 A1    May 5, 2011

Related U.S. Application Data

(60) Provisional application No. 61/075,046, filed on Jun. 24, 2008.

(51) Int. Cl.
*A46B 9/04* (2006.01)
*F16C 35/00* (2006.01)

(52) U.S. Cl.
USPC ............... 15/22.2; 15/167.1; 15/22.1

(58) Field of Classification Search
USPC ............................ 15/167.1; 384/24
IPC .................. A46B 9/04; F16C 35/00
See application file for complete search history.

(56) References Cited

U.S. PATENT DOCUMENTS

| | | | |
|---|---|---|---|
| 4,180,766 A | 12/1979 | Matula | |
| 4,607,492 A * | 8/1986 | Demus et al. | 62/55.5 |
| 7,315,098 B2 | 1/2008 | Kunita et al. | |
| 7,328,474 B2 * | 2/2008 | Nishinaka et al. | 15/22.2 |
| 2010/0277013 A1* | 11/2010 | Jungnickel et al. | 310/37 |

FOREIGN PATENT DOCUMENTS

| | | |
|---|---|---|
| DE | 2242825 A1 | 3/1974 |
| GB | 1374319 A | 11/1974 |
| JP | 48088072 U | 10/1973 |
| JP | 04370413 A | 12/1992 |

* cited by examiner

*Primary Examiner* — Monica Carter
*Assistant Examiner* — Stephanie N Berry

(57) ABSTRACT

The linear bearing is useful in a personal care appliance and includes an elongated center member (14) having end elements (20, 22) at each end thereof, the center member having an arm (16) with a workpiece (18) at the free end thereof. Two sets of orthogonal leaf springs (24, 38) are positioned in the vicinity of the ends of the center assembly, one end of each leaf spring in each set connected to an associated end member, the other end of each leaf spring in each set connected to a fixed-position member (26, 40), such as the housing (37) of the appliance.

6 Claims, 9 Drawing Sheets

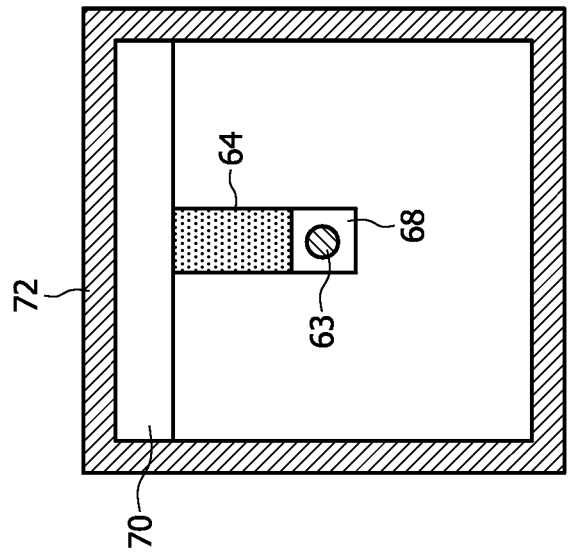
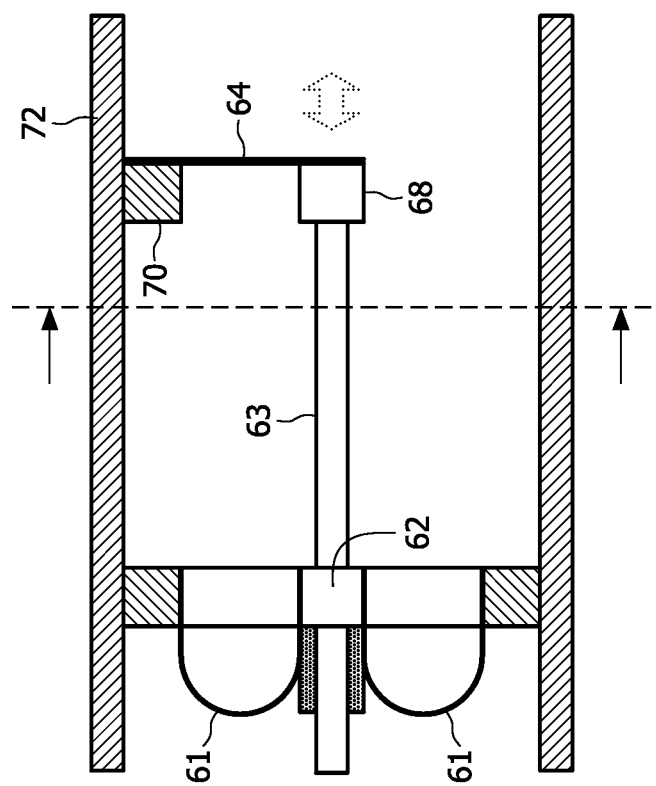
FIG. 6A
FIG. 6B

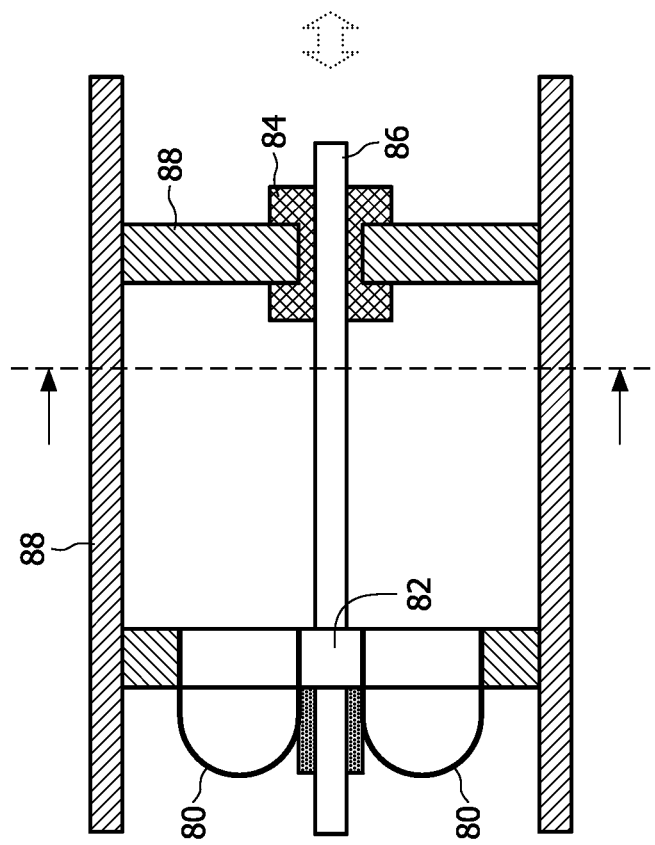
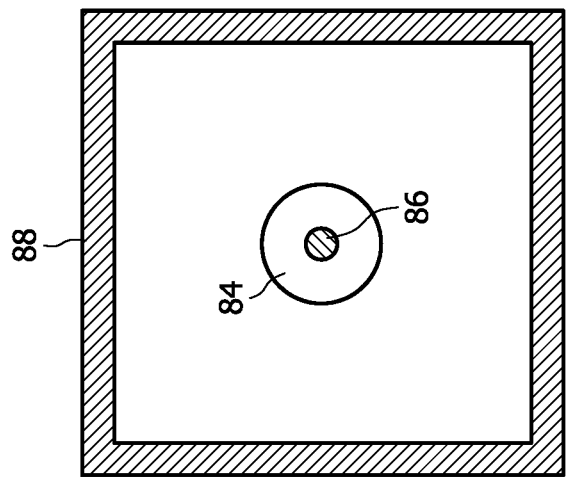
FIG. 7A
FIG. 7B

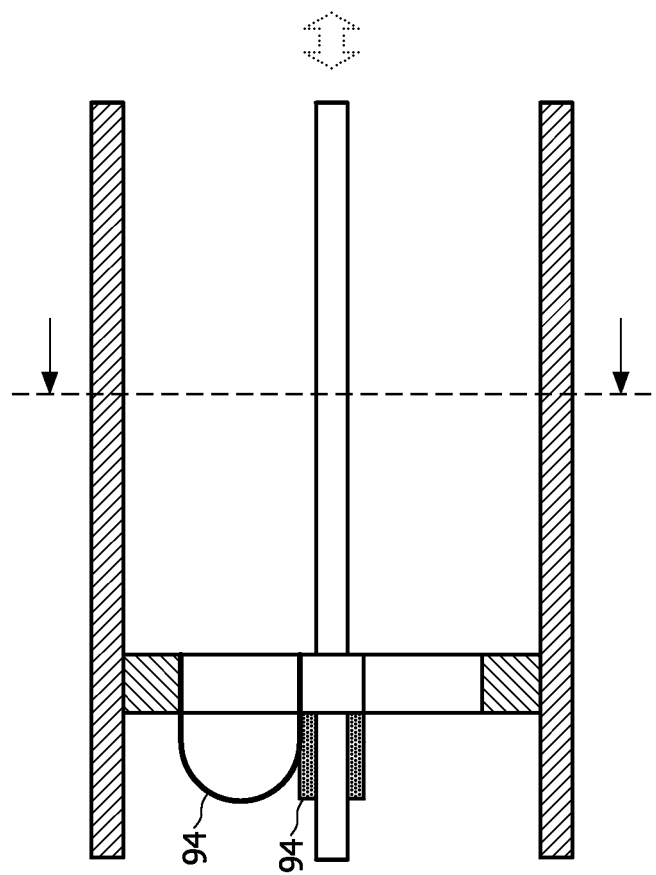

LINEAR BEARING USING ROLLING LEAF SPRINGS

This invention is directed generally to linear bearings, and more specifically concerns a linear spring bearing.

Linear bearings have been and are used in various applications, including linear drive motors, which are used in a variety of small appliances. Common types of linear bearings are ball bearings and bushings. While each of these types of bearings have their own advantages, and are useful in particular applications, they also have significant disadvantages in many applications, including a small amount of play which results in noisy operation, particularly at higher frequencies with a reciprocating motion. Such bearings also typically have a significant amount of friction, which in some applications can be alleviated by use of lubricants, but in other applications, such as those involving a resonant system, result in a significant loss of efficiency.

Spring bearings are also commonly used to overcome some of the disadvantages of traditional linear bearings. Spring bearings generally have very little play and there is no friction. However, spring bearings have a substantial spring rate and a range of motion dependent upon the size of the spring. Spring bearings are not particularly useful in a resonant system used in many applications, since a change in the spring rate, caused for instance by a change in load on the system, will result in a change of the resonant response of the system, which is undesirable. Any arrangement which compensates for spring rate change, however, will necessarily increase the complexity and cost of the overall system.

Hence, it would be desirable to have a linear bearing which is without significant play or friction, with a desired range of motion, and with little or no spring rate. Such a linear bearing would be particularly desirable in a reciprocating linear drive appliance, such as a toothbrush or a shaver.

Accordingly, a linear bearing is disclosed which comprises: a center member assembly having a workpiece assembly mounted thereto; one set of leaf springs, one end of each leaf spring being connected to the center member assembly, the other end thereof being connected to a fixed-position member, wherein the leaf springs are arranged such that there is approximately a 180° bend between the two ends thereof; and (a) a spring member or (b) another set of leaf springs connected to the other end of the center member assembly or (c) a bushing supporting the other end of the center member, and connected to said fixed-position member, or to another fixed-position member, wherein in operation, the one set of leaf springs and the spring member or said another set of leaf springs move back and forth in a reciprocal linear motion, along with the center member assembly and the workpiece assembly.

FIGS. 6A and 6B are longitudinal and lateral cross-sectional views of an alternative embodiment.

FIGS. 7A and 7B are longitudinal and lateral cross-sectional views of another alternative embodiment.

FIGS. 9A and 9B are longitudinal and lateral cross-sectional views of another embodiment.

Figure 1A:
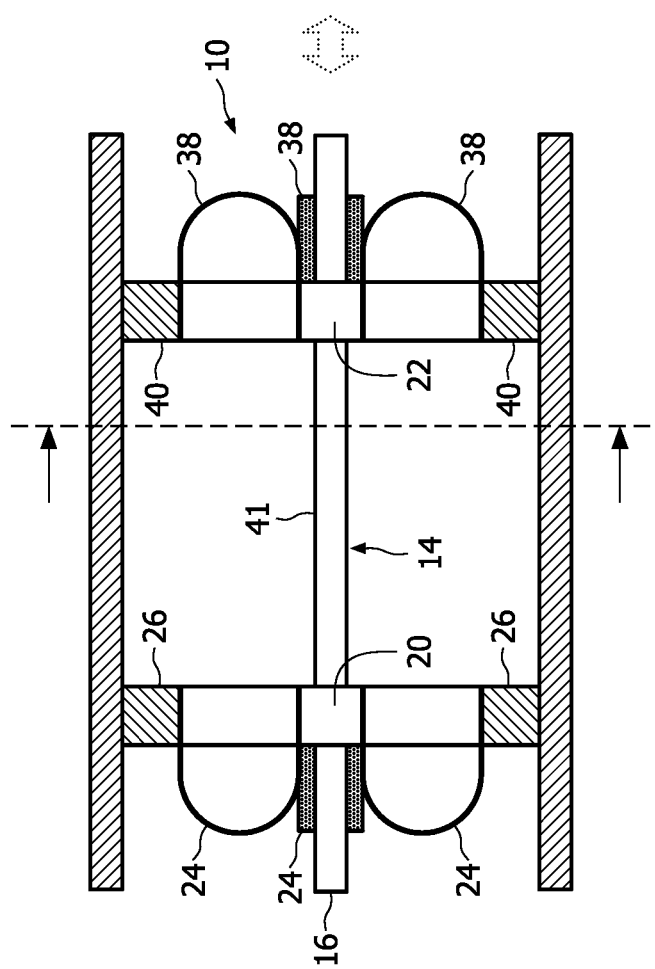
FIGS. 1A and 1B are longitudinal and lateral cross-sectional views of one embodiment of the linear bearing of the present invention.
Figure 1B:
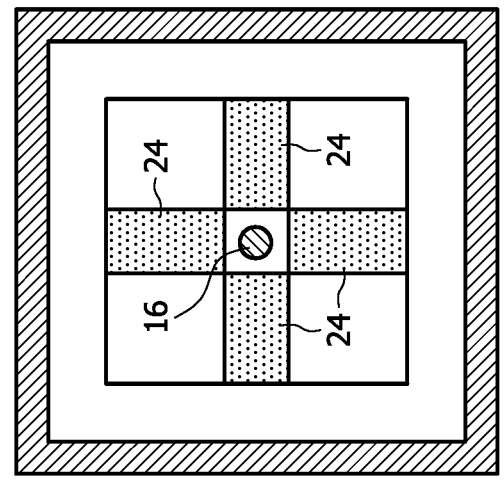
Figure 2:
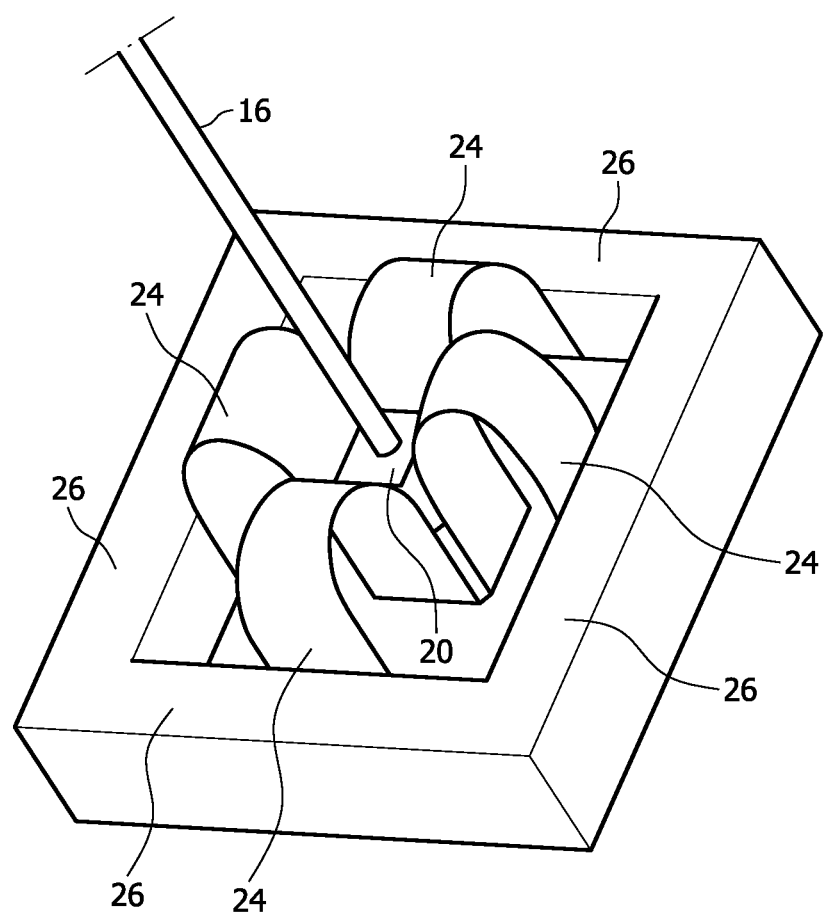
FIG. 2 is a simplified perspective view of a portion of the linear bearing of FIGS. 1A and 1B.
Figure 3:
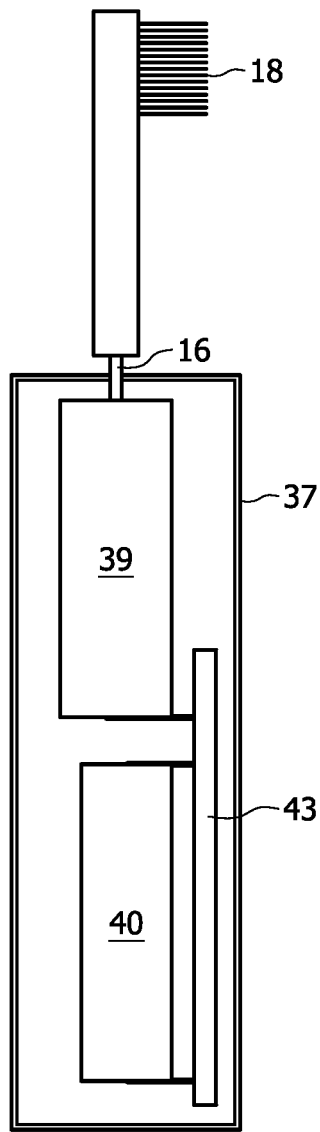
FIG. 3 is an elevational view of a toothbrush application using the linear bearing of FIG. 1.
Figure 4:
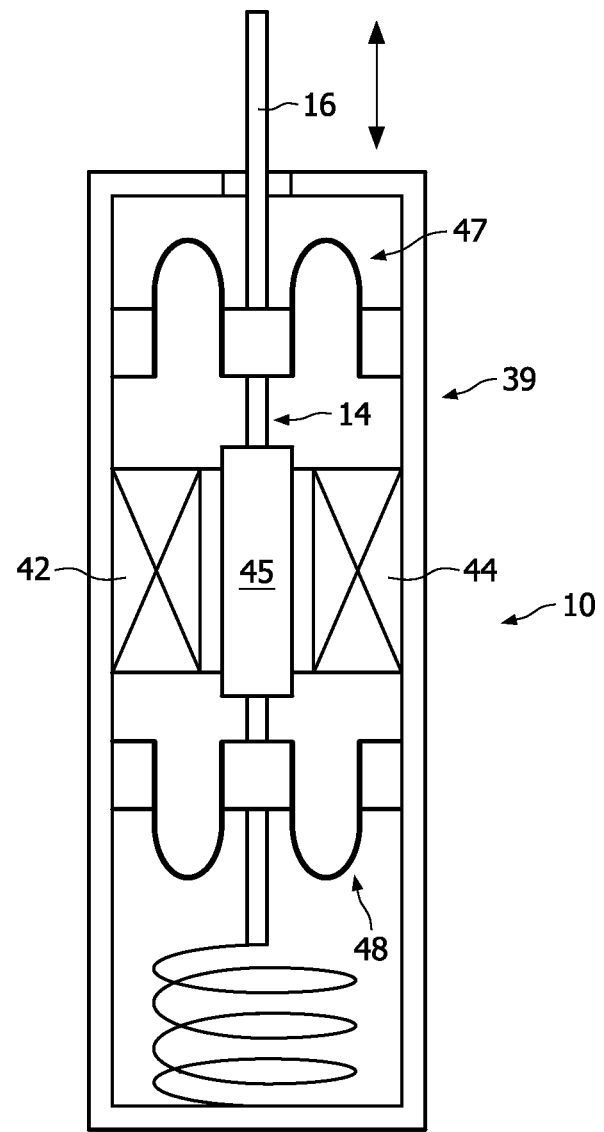
FIG. 4 is an elevational view of a portion of the structure of FIG. 3.
Figure 5:
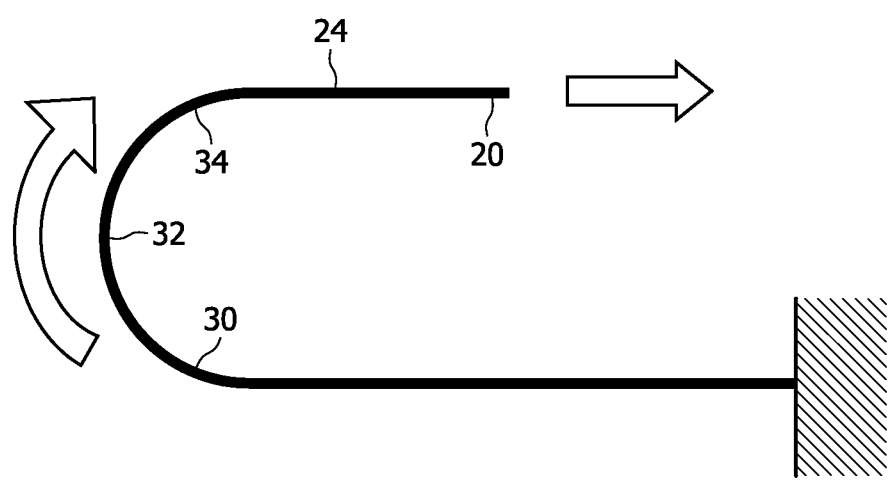
FIG. 5 is a simplified view of a single spring portion of the linear bearing.

FIGS. 1A and 1B and 2 show one embodiment of the linear bearing, referred to generally at 10, disclosed herein. FIGS. 3 and 4 show the linear bearing 10 in a power toothbrush application. It should be understood, however, that the linear bearing has applications in a variety of other personal care appliances, such as, for instance, shavers and power flossers and hair trimmers. FIG. 5 shows the operation of a single spring portion of the linear bearing. The linear bearing 10 includes a central mounting assembly 14, which in turn includes two opposing, substantially identical end members 20 and 22. Extending from one end member 20 of mounting assembly 14 is a workpiece arm 16, at the end of which is mounted a brushhead 18 (FIG. 3) designed and arranged to be suitable for brushing human teeth.

In FIGS. 1, 2A, 2B and 3-4 the mounting assembly 14 is approximately 50 mm long and is made from steel or similar strong material. Connected between each end member (20 for instance) and an associated fixed ground point member 26, which is attached to the appliance housing, are leaf spring members 24-24, also referred to as roller leaf springs. The ground members 26-26 could also be an integral part of or the housing per se. In the embodiment shown, there are four such leaf spring members, for each end member, at orthogonal positions, i.e. spaced 90° apart. In the embodiment shown, the leaf spring members are made from straight strip spring material, such as pliable spring steel. Other highly elastic material could be used, including metal other than steel or plastic.

The orthogonal spring arrangement has the required spring stiffness in all directions necessary for a linear bearing. In the embodiment shown, the thickness of the spring member for a toothbrush application is 0.01-0.3 mm, with a preferred thickness of 0.05 mm. The width of the spring is 1-5 mm with a preferred width of 3 mm, while the length is 5-30 mm, with a preferred length of 10 mm.

Each leaf spring member, while straight in its relaxed position apart from the arrangement shown, is bent 180° in its operative position to provide the shape shown in the figures, including FIG. 5. The deformation of the spring member is elastic so that the spring returns to its original flat shape if released. In operation, axial movement of the mounting assembly 14, as shown by the arrow in FIG. 1, and hence movement of end member 20, will result in area 30 of the spring bending, with the spring deforming, i.e. rolling, in spring area 32. The spring will relax in spring area 34.

In the embodiment shown, a similar set of four orthogonal spring members 38-38 are attached to opposing end member 22 and opposing ground point members 40-40, which could also be attached to the housing or form part of the housing. In the embodiment shown, the two sets of ground members 26-26 and 40-40 are connected to the housing and are thereby in effect connected together. As indicated above and as shown in the figures, the two end members 20 and 22 are also connected together, by a central member 41. The workpiece arm 16 could be an extension of central member 41. Members 41, 20, 22 and 16 could also be an integral, single-piece assembly.

In this double-ended spring arrangement, with a set of four leaf springs at both ends of mounting assembly 14, the theoretical net energy required for reciprocal motion of the system is zero, resulting in a zero spring rate. This has advantages for many commercial applications, particularly resonant applications, including a toothbrush, since differing loads on a brushhead, which occur during normal brushing, will not affect the spring rate of the linear bearing system, and hence will not affect the resonant operation of the system. The system shown also has significant lateral stiffness while permitting a relatively large range of axial motion, which is desirable for a toothbrush application, without the need for an excessively large spring. Further, since the springs deform in their center areas, and not at their end attachments, the chances of the spring breaking at the end attachments, which is typical in spring systems, is relatively low. It should also be understood that the spring system disclosed herein can be made in various sizes, for differing applications, from quite small to fairly large.

The linear bearing can be driven by various arrangements, including a magnetic arrangement, which is shown in FIGS. 2 and 3 for a toothbrush application, which in FIG. 2 includes a housing 37, a drive train assembly 39, a battery 40 and an electronic driver/control 43. The drive train assembly 39 includes opposing electromagnets 42, 44 provided within housing 37 which interact with permanent magnets 45 located on the mounting assembly 14. As the electromagnets are driven by an AC signal source (electronic driver/control) 43, the resulting interaction with the permanent magnets 45 produces a back-and-forth (linear) action, shown by the arrows, of the mounting assembly 14 as well as forward and rear linear bearings 47 and 48, arranged as described above. Connecting the rear end of the mounting assembly 14 to the housing is a resonant spring 49. The ratio of the resonant spring 49 and the inertia of the mounting assembly 14 defines the resonant frequency of the appliance. One additional advantage to this arrangement is that it can operate at sonic frequencies in a resonant mode, for instance, within the range of 250-270 Hz, at high efficiency.

Figure 10A:
FIGS. 10A-10D show a variety of shapes for the spring member portion of the linear bearing.
Figure 10B:
Figure 10C:
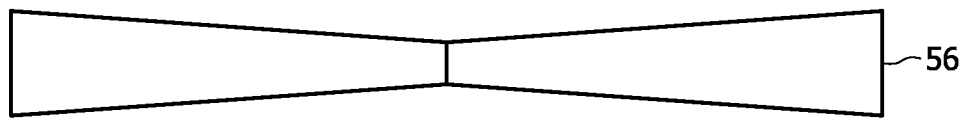
Figure 10D:
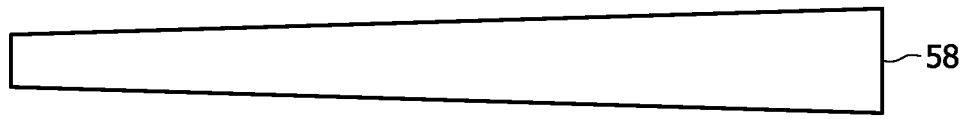

The individual spring members can have various outline configurations, such as shown in FIGS. 10A-10D. Spring 50 in FIG. 10A is like that shown in FIGS. 1-5, i.e. a spring having straight sides. FIG. 10B shows an alternative shape for a spring 51 in which the spring is slightly larger in width at its center than at the ends thereof, again with straight sides. Such a spring operates like a centering spring, permitting long travel without any additional play. FIG. 10C shows a spring 56 which has a reduced width at its center compared to its ends, with straight sides extending from the center to the ends of the spring. This spring shape results in an off-center motion for the workpiece, focusing on one side of the workpiece travel or the other. FIG. 10D shows another arrangement, in which the spring 58 has straight sides, with the width of the spring increasing from one end to the other. The springs can also have curved sides. Various spring response curves are possible by modifying the shape and/or varying the thickness of the leaf springs. The springs in each particular set need not be all the same shape, although preferably they are, particularly opposing springs.

FIGS. 6A, 6B show an embodiment with a single set of four leaf springs 61 attached to one end 62 of mounting assembly 63, with a conventional single flat leaf spring 64 at the other end of the mounting assembly, connected between its corresponding end member 68 and ground point member 70, which is connected to a housing 72. The positions of the set of leaf springs 61 and the conventional leaf spring 64 can also be reversed from that shown in FIGS. 6A and 6B in another arrangement.

FIGS. 7A and 7B show another embodiment with a single set of four leaf springs 80 attached to one end 82 of the mounting assembly and a bushing 84 at the other end 86 thereof. Bushing 84 is mounted in a ground member 88 which is attached to the housing 88.

Figure 8B:
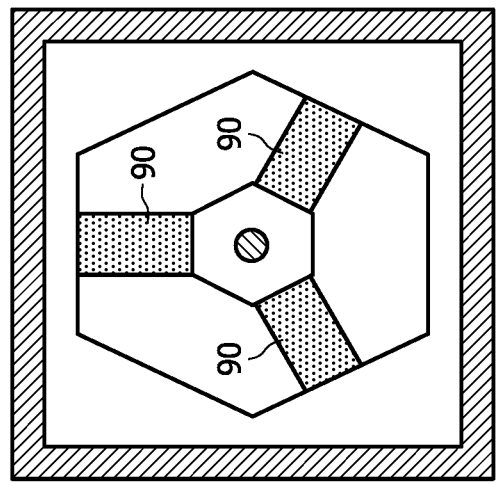
FIGS. 8A and 8B are longitudinal and lateral cross-sectional views of a still further embodiment.
Figure 8A:
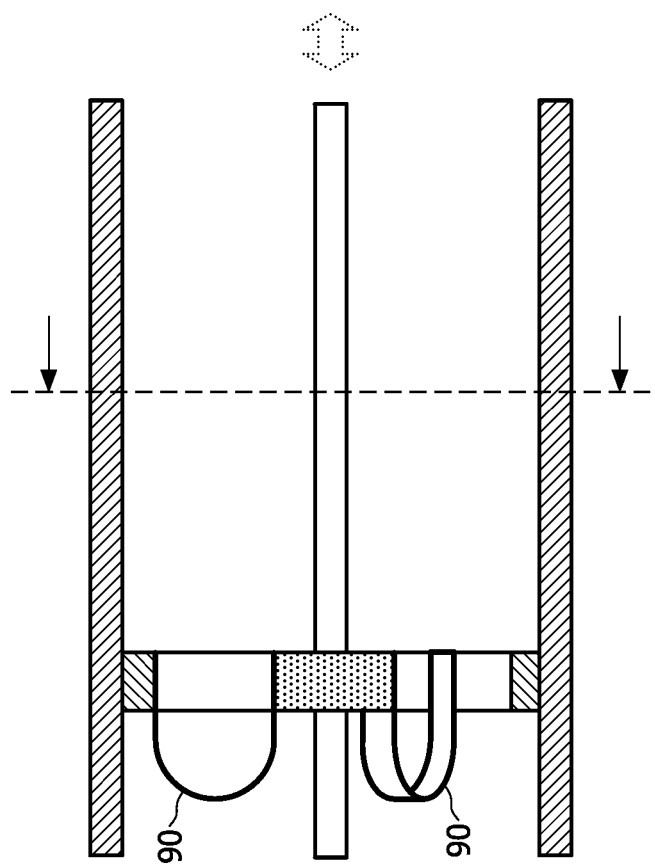

FIGS. 8A, 8B and 9A, 9B show other embodiments. In FIGS. 8A and 8B, three springs 90-90 are used instead of four, and are positioned at equally spaced positions of 120°. This arrangement provides a substantially similar effect to the four spring embodiment. FIGS. 9A, 9B show a two spring arrangement, in which springs 94-94 are positioned at 90° to each other. This has a somewhat different action, since the two springs are not opposed, but it still has many of the advantages of the other embodiments.

All of the above alternative spring arrangements can be implemented in a dual set (at both ends of the mounting member) or in a single set at one end of the mounting member with a conventional bearing member (flat leaf spring or bushing) at the other end.

Accordingly, a linear bearing has been disclosed which is useful in a variety of commercial applications. The linear bearing has very little play and substantially no friction in operation. Furthermore, the bearing, using a plurality of roller leaf springs, has substantially zero spring rate. Such bearings are convenient and useful in a variety of personal care appliance applications, in particular, a power toothbrush.

Although a preferred embodiment of the invention has been disclosed for purposes of illustration, it should be understood that various changes, modifications and substitutions may be incorporated in the embodiment without departing from the spirit of the invention which is defined by the claims which follow.

The invention claimed is:

1. A resonant drive power toothbrush using linear bearings, comprising:

a center member assembly (14) having a brushhead assembly (16, 18) for the power toothbrush mounted thereto;

one set of four equally spaced leaf springs (24), one end of each leaf spring being connected to the center member assembly in the vicinity of one end thereof, the other end of each leaf spring assembly being connected to a fixed-position member (26), wherein the leaf springs are arranged such that there is approximately a 180° bend between the two ends thereof; and another set of four equally spaced leaf springs (38) connected to the other end of the center member assembly or supporting the other end of the center member, and connected to said fixed-position member, or to another fixed-position member (40), wherein in operation, the two sets of leaf springs are configured and mounted and arranged to have a range of axial motion and sufficient lateral stiffness and are driven so as to move back and forth in a reciprocal linear motion, suitable for a power toothbrush, along with the center member assembly and the brushhead assembly wherein the two sets of leaf springs are arranged and configured so that the theoretical net energy required for reciprocal motion of the brushhead assembly is zero, resulting in a zero spring rate.

2. The linear bearing of claim 1, wherein the leaf springs have a thickness in the range of 0.01-0.3 mm, a length within the range of 5-30 mm and a width within the range of 1-5 mm.

3. The linear bearing of claim 1, wherein at least some of the leaf springs (50) have straight side edges and have the same width from end to end.

4. The linear bearing of claim 1, wherein at least some of the leaf springs (58) have straight side edges increasing in width from end to end.

5. The linear bearing of claim 1, wherein at least some of the leaf springs (51) are wider at the midpoint than at the respective ends thereof.

6. The linear bearing of claim 1, wherein at least some of the leaf springs (56) are narrower at the midpoint than at the respective ends thereof.

\* \* \* \* \*